US00PP29777P3

(12) United States Plant Patent
Fourie

(10) Patent No.: US PP29,777 P3
(45) Date of Patent: Oct. 30, 2018

(54) PLUM TREE NAMED 'POLARIS'

(50) Latin Name: *Prunus salicina*
Varietal Denomination: Polaris

(71) Applicant: STARGROW CULTIVAR DEVELOPMENT (PROPRIETARY) LIMITED, Stellenbosch (ZA)

(72) Inventor: Jeanne Fourie, Stellenbosch (ZA)

(73) Assignee: STARGROW CULTIVAR DEVELOPMENT (PROPRIETARY) LTD., Stellenbosch (ZA)

( * ) Notice: Subject to any disclaimer, the term of this patent is extended or adjusted under 35 U.S.C. 154(b) by 133 days.

(21) Appl. No.: 15/330,097

(22) Filed: Aug. 5, 2016

(65) Prior Publication Data

US 2018/0042154 P1 Feb. 8, 2018

(51) Int. Cl.
*A01H 5/08* (2018.01)
*A01H 6/74* (2018.01)

(52) U.S. Cl.
USPC ..... Plt./184
CPC ..... *A01H 6/7472* (2018.05); *A01H 5/08* (2013.01)

(58) Field of Classification Search
USPC ..... Plt./184, 180
CPC ..... A01H 5/0862; A01H 5/0837; A01H 5/08; A01H 6/7472
See application file for complete search history.

(56) References Cited

U.S. PATENT DOCUMENTS

PP13,121 P2 * 10/2002 Bubani ..... A01H 5/0862 Plt./184
PP26,175 P3 * 12/2015 Bacon ..... A01H 5/0862 Plt./184
PP28,596 P3 * 11/2017 Bradford ..... Plt./184

OTHER PUBLICATIONS

University of California Fruit Report 2018, retrieved on Feb. 7, 2018, retrieved from the Internet at http://ucanr.edu/sites/fruitreport/Rootstocks/Search_Name/?uid=33&ds=538#, 2 pp. (Year: 2018).*

* cited by examiner

*Primary Examiner* — June Hwu
(74) *Attorney, Agent, or Firm* — Kilpatrick Townsend & Stockton LLP

(57) ABSTRACT

'Polaris' is new plum tree variety that can be distinguished from other plum tree varieties by a combination of characteristics that include harvesting date, flesh color, fruit shape, and eating quality.

4 Drawing Sheets

Genus and species: The plum tree variety of this invention is botanically identified as *Prunus salicina*.

Variety denomination: The variety denomination is 'Polaris'.

BACKGROUND OF THE INVENTION

The invention refers to a new plant variety of plum tree (*Prunus salicina*) named 'Polaris'. The new *Prunus* variety is product of a planned and controlled breeding program for new *Prunus* varieties. The objective of the breeding program is to select new high quality *Prunus* varieties with good production and outstanding eating quality The new *Prunus* variety was obtained through an open pollinated cross, in which the seed and pollen parent are both unknown. Seedlings of the population were planted on own root in 1999. The first fruit of 'Polaris' was observed in 2003 from a seedling tree. Buds from the seedling were retrieved and asexually reproduced by top-grafting/budding onto rootstock of 'Marianna 1929' in Clanwilliam, Western Cape, South Africa. Five trees were produced as second generation trees in 2005. Fruit from the second generation trees was first observed in 2008. 'Polaris' was selected in 2009 after the second fruit crop from the second generation trees for further development because of the unique fruit quality traits observed over the two seasons consecutively.

BRIEF SUMMARY OF THE INVENTION

The following traits have been repeatedly observed and are determined to be unique characteristics of 'Polaris' which in combination distinguish this plum tree as a new and distinct variety:

1. Harvesting date;
2. Flesh color;
3. Fruit shape; and
4. Eating quality.

The fruit of 'Polaris' ripens between 'Fortune' and 'Flavor King' (U.S. Plant Pat. No. 8,026). Compared to "Fortune", fruit from 'Polaris' ripens 10 days after "Fortune". Compared to 'Flavor King', fruit of 'Polaris' develops a yellow flesh color with some red bleeding distinctly from the skin while fruit of 'Flavor King' has pinkish red flesh. Fruit of 'Polaris' has a truncate to depressed apex where the apex of 'Flavor King' fruit is rounded.

Fruit of 'Polaris' has unique eating quality. The orange-pink flesh is firm non-melting with a "rose-water" type flavor and a high sugar content.

BRIEF DESCRIPTION OF THE PHOTOGRAPHS

The accompanying photographs illustrate the appearance of the new plum tree in production, fruit and internal quality of the fruit. The color of the photographs might vary slightly compared to the variety description, however the botanical description are the most accurately description of the true color of this new variety.

Figure 1:
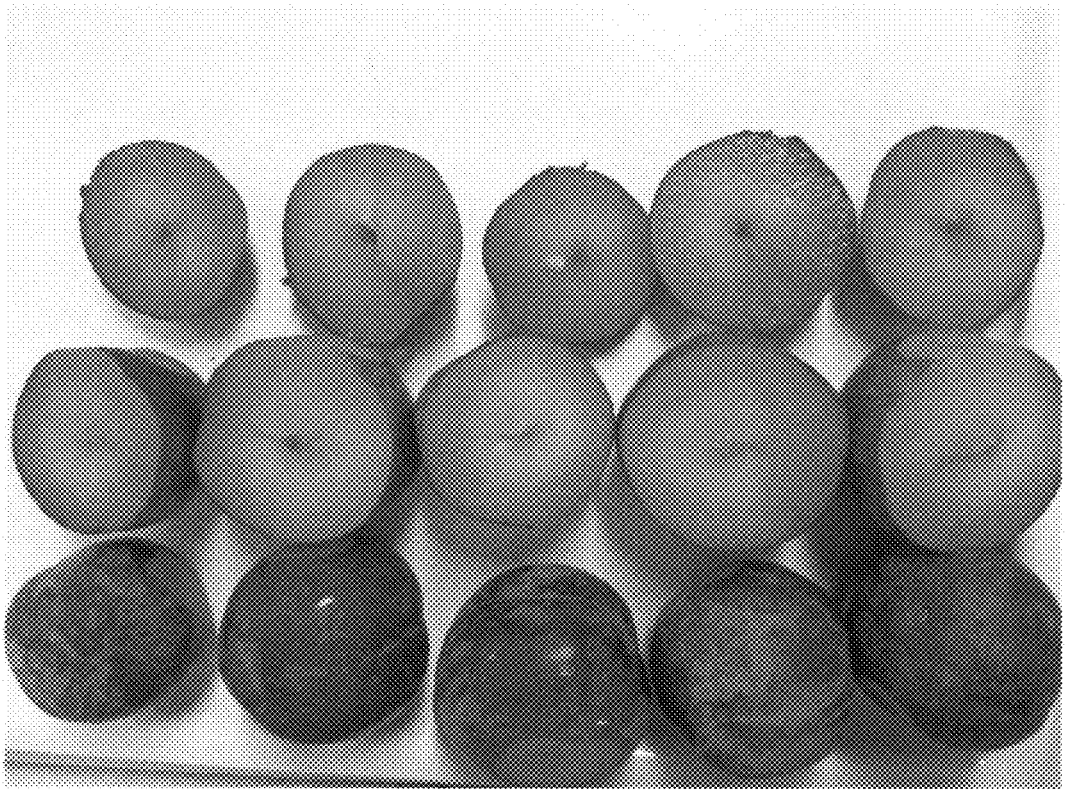

FIG. 1. A central axis cut of fruit illustrating the yellow flesh with bleeding in the flesh.

Figure 2:
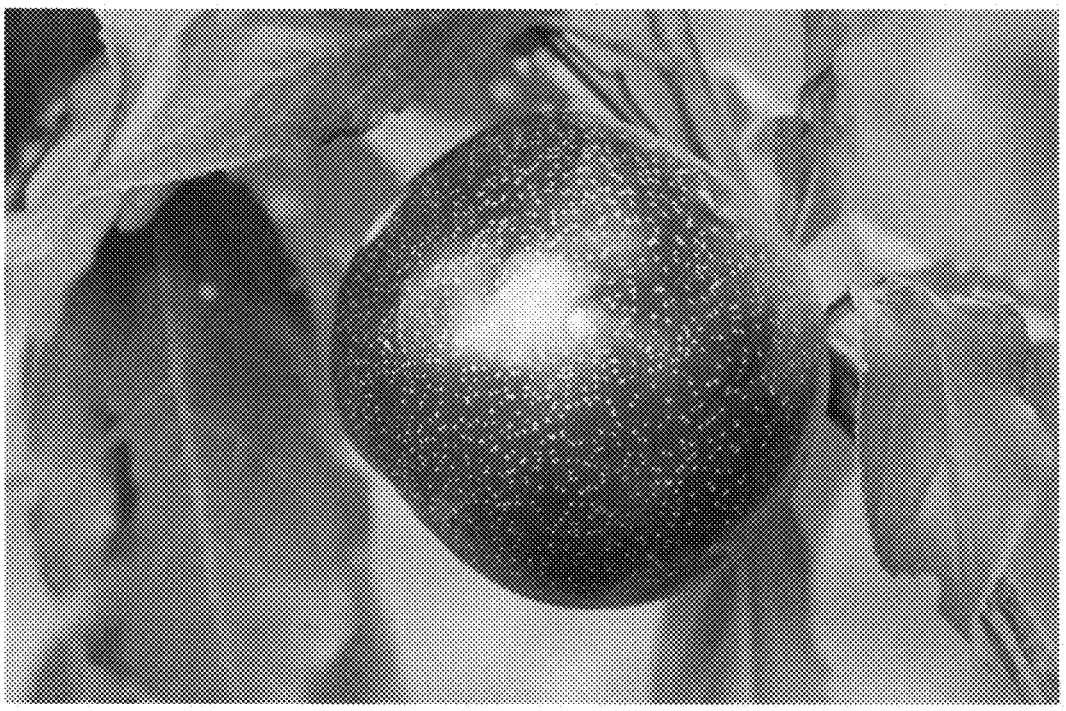

FIG. 2. A fully developed fruit, close up, on a tree grown in an orchard, illustrating colour development and shape of the fruit.

Figure 3:
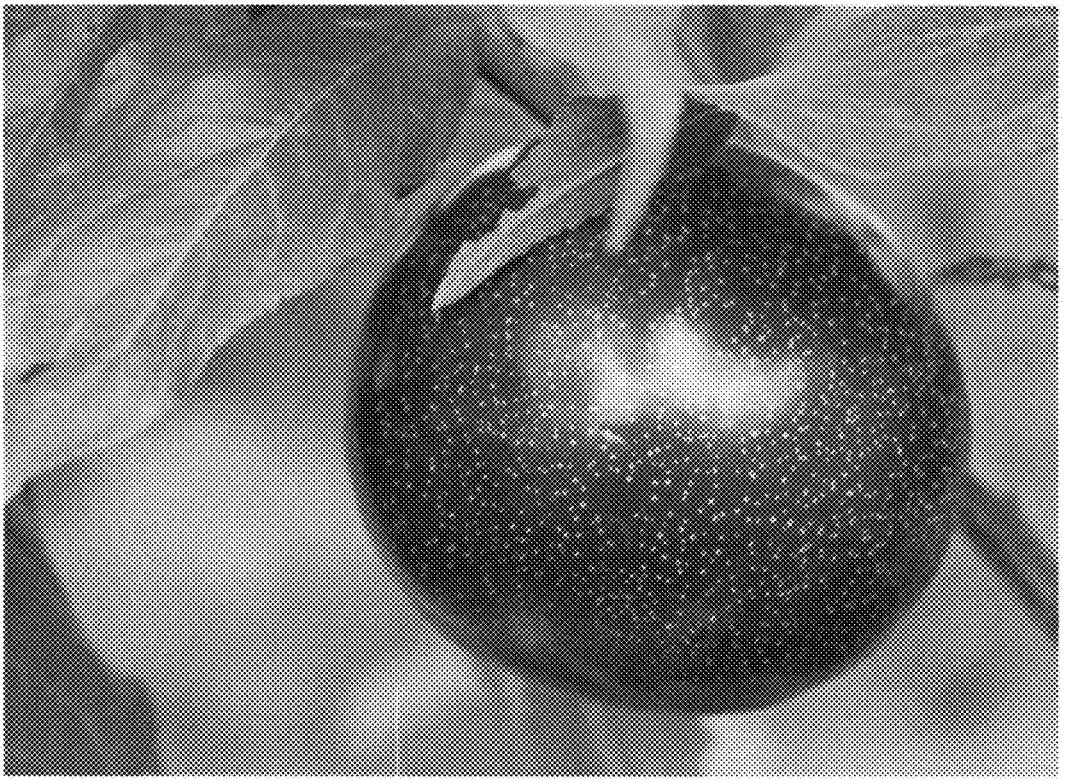

FIG. 3. A fully developed fruit, close-up, on a tree grown in an orchard illustrating the colour development and shape of this new variety.

Figure 4:
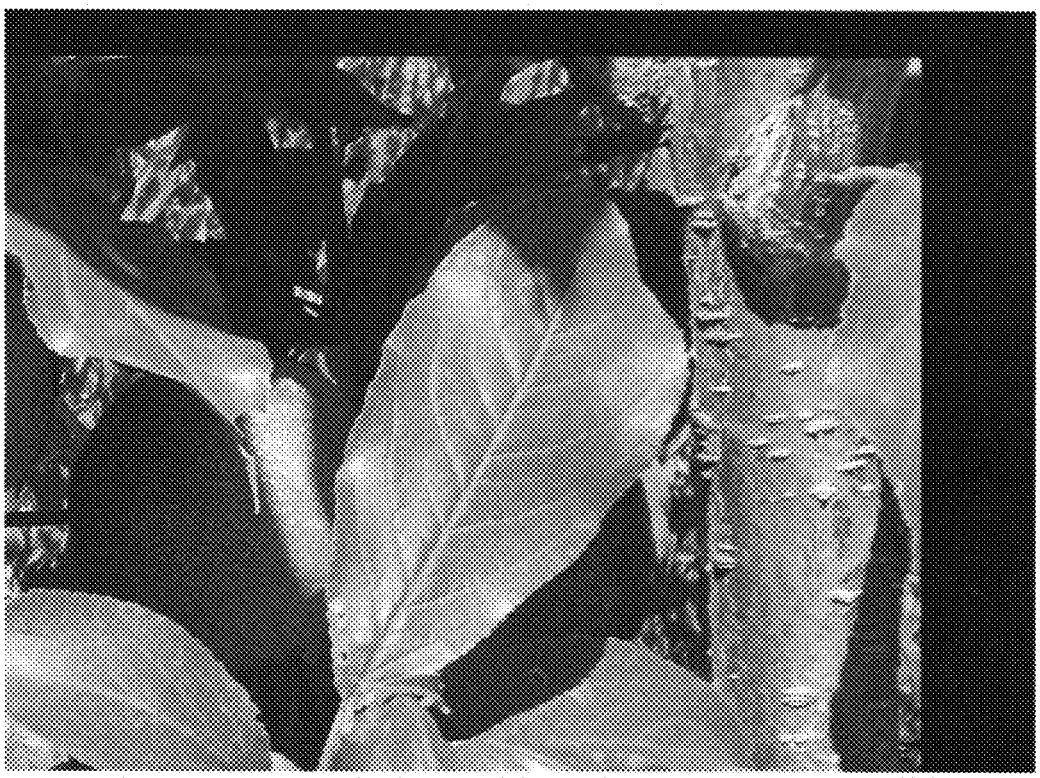

FIG. 4. Fully developed leaf illustrating the color, shape of the leaf and margin incisions.

Figure 5:
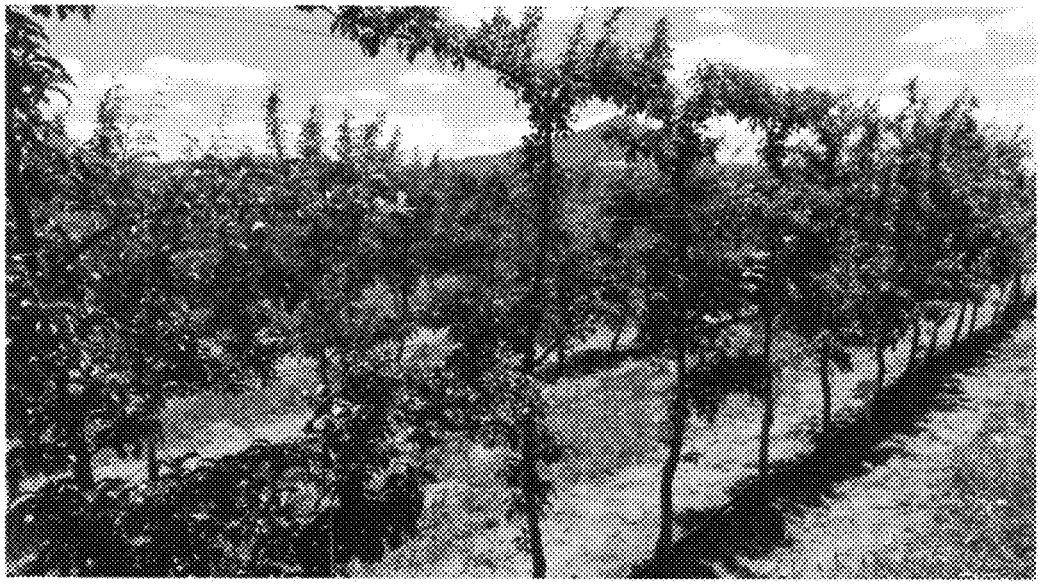

FIG. 5. Illustrates a four year old growing tree on a trellis system of this new variety in an orchard.

Figure 6:
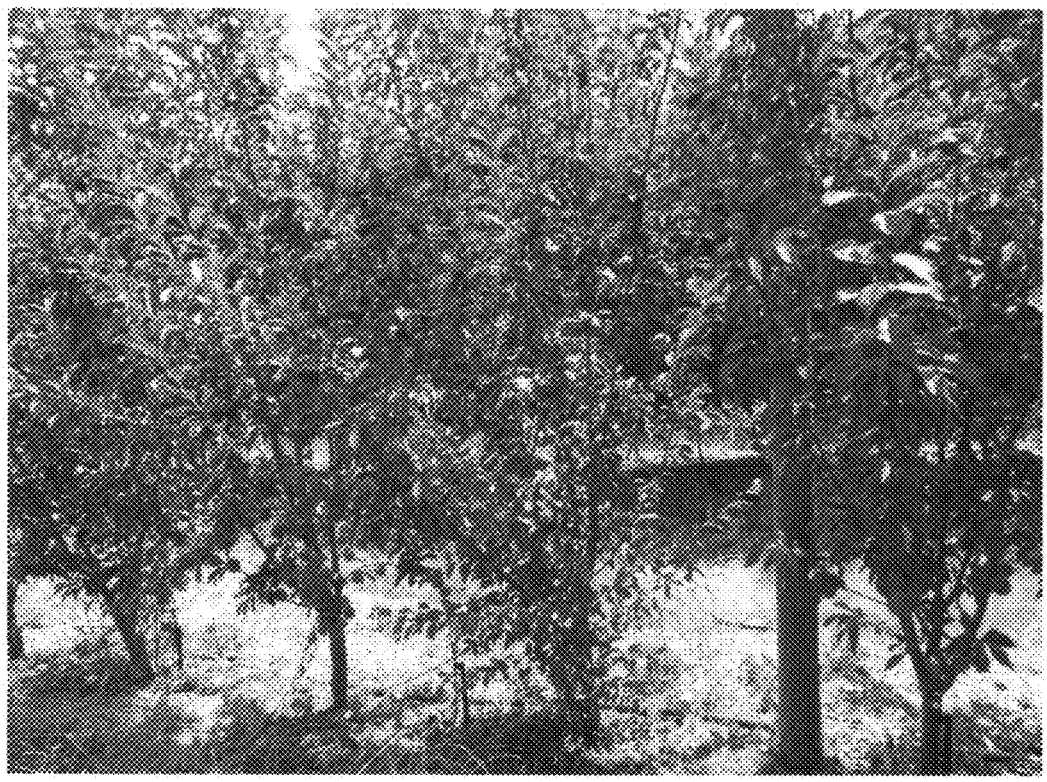

FIG. 6. Illustrates a bearing tree in a natural growing state.

DETAILED BOTANICAL DESCRIPTION

The new *Prunus* variety 'Polaris' has not been observed under all possible environmental conditions. The phenotype of the new variety may vary with variations in environmental conditions such as temperature, light intensity and day length without any change in the genotype of the tree.

The photographs and description is taken from trees grown at the Martinusrust Farm situated near Clanwilliam in the Western Cape, South Africa. General commercial orchard practice is applied to the trees. The climate is temperate continental with low temperatures during winter and high temperatures during summer. The soil type is sandy with a double drip irrigation system.

The detailed botanical description is taken from over several fruiting season of trees budded on a standard plum rootstock. The trees were four years old on a trellis system when the first observations were made. Measurements and numerical values represents averages for typical plants and plant parts. The actual measurements of any individual plant of plant parts, or any group of plants of plant parts, may vary from the stated average. Reference to colors are based on The Royal Horticultural Society Color Chart, 5th Edition, 2007.

PLANT DESCRIPTION

General:

- *Size*.—Medium, approximately 1.5 m spread and 3 m height.
- *Vigor*.—Medium.
- *Growth*.—Upright.
- *Productivity*.—Productive/good.
- *Form*.—Pyramid.
- *Bearer*.—Regular bearer.
- *Fertility*.—Self — unfruitful; pollinator required for optimal production. Mid-blooming season.
- *Disease resistance/susceptibility*.—No particular plant/fruit resistance/susceptibility has been observed.
- *Insect resistance/susceptibility*.—No particular plant/fruit resistance/susceptibility has been observed.
- *Hardiness*.—Produces well on evaluation site in Robertson, South Africa with ±200 Richardson cold units.

Trunk:

- *Circumference*.—Approximately 17 cm, measured +−40 cm above ground.
- *Color*.—Brown Group N200B.

Branch:

- *Length*.—Approximately 206 cm (2 branches), 116 cm (1 branch).
- *Size*.—Diameter approximately 7 cm (measured +−30 cm from trunk).
- *Texture*.—Smooth-Medium on young wood increasing roughness with age.
- *Color*.—Brown Group N200B.

Lenticels:

- *Density*.—Count, approximately 21 lenticels within a 2 $cm^2$ area on the trunk.
- *Density*.—Count, approximately 31 lenticels within a 2 $cm^2$ area on the branch.
- *Color*.—Both trunk and branch, Brown Group N200D.
- *Size*.—Trunk lenticels approximately 5 $mm^2$; Branch lenticels approximately 0.9 $mm^2$.
- *Length*.—Trunk approximately 5 mm; Branch approximately 1.63 mm.
- *Width*.—Trunk approximately 1 mm; Branch approximately 0.57 mm.
- *Number of lenticels*.—Present, medium.

Flowering shoots:

- *Size (diameter)*.—Approx. 4.25 mm.
- *Colour*.—Brown Group N200D.
- *Internode length*.—Approx. 23.3 mm.
- *Flowering shoot lenticels*.—About 11 per $cm^2$; Color: N170B.
- *Flowering shoot leaf buds (shape, width, length, and colour)*.—Shape: Acute. Width: Approx. 1.73 mm. Length: Approx. 3.55 mm. Colour: Dark greyed — 177A.
- *Flowering shoot flower buds (shape, width, length, colour and number of buds per node)*.—Shape: Obtuse. Width: Approx. 1.90 mm. Length: Approx. 2.74 mm. Colour: Dark Greyed — 177A. Number of buds per node: Usually 3.
- *Density of flower buds*.—Usually 2-4 per node.
- *Density of leaf buds*.—Usually 1 per node.
- *Flower bud distribution*.—On spurs and on one year old shoot.
- *Ratio of wood (leaf) buds to flowering buds*.—Usually 1:2 on node.
- *Anthocyanin intensity*.—None — White petals.
- *Spurs length*.—Approx. 6.4 mm.
- *Vegetative bud size*.—Width — Approx. 1.53 mm; Length — Approx. 3.3 mm.

FLOWER DESCRIPTION

General:

- *Flower blooming period*.—First bloom approximately $5^{th}$ September in Paarl/Stellenbosch area, Western Cape, RSA. Full bloom approximately 16 September in Paarl/Stellenbosch area, Western Cape, South Africa.
- *Location of first bloom*.—Spurs.
- *Location of full bloom*.—Uniform throughout the canopy.
- *Time of bloom*.—Approximately 5-16 September.
- *Duration of bloom*.—Medium, Approximately 12 days.
- *Diameter of fully opened flower (width)*.—Approximately 20 mm.
- *Aroma*.—Slight.

Flower buds:
*Length*.—Approximately 2.5 mm.
*Shape*.—Pointy.
*Pubescence*.—Absent.
*Color*.—Greyed orange group — 177A.

Petals:
*Average size* (*length & diameter*).—Length — 9 mm; Diameter — 7.5 mm.
*Arrangement*.—Free.
*Shape*.—Obovate.
*Number*.—5.
*Apex shape*.—Rounded.
*Base shape*.—Narrow at point of attachment.
*Color of inner and outer surface*.—White group — NN155D.
*Frequency of flowers with double petals*.—Almost none.
*Claw length*.—0.60 mm.
*Margin waviness*.—Even margin, no waviness.
*Base angle*.—Cornered, narrowing to claw forming.
*Pubescence of inner and outer surface*.—Absent.

Sepals:
*Number*.—5.
*Length*.—Approx. 2.95 mm.
*Diameter*.—Approx. 2 mm.
*Shape*.—Oblong-elongated.
*Color*.—Green Group 135D.
*Surface texture*.—Smooth.
*Positioning*.—Between petals, when petals are fully open.
*Pubescence of inner surface*.—Absent.
*Pubescence of outer surface*.—Absent.
*Frequency of flowers with double sepals*.—Absent.
*Apex shape*.—Rounded.
*Base shape*.—Broad.

Peduncle:
*Length*.—Approximately 5.4 mm.
*Diameter*.—Approximately 0.88 mm.
*Color*.—Green Group 135D.
*Pubescence*.—Absent.

Stamens:
*Number*.—Average 30.
*Length*.—Approximately 6.55 mm average.
*Filament color*.—White group — NN155D.
*Anther color*.—Greyed Orange Group — 164C.
*Flower pollen color*.—Greyed Orange Group — 165B.

Pistil:
*Number*.—1.
*Length*.—Approximately 7.50 mm average.
*Pubescence*.—Absent.
*Stigma extension in comparison to anthers*.—Level or slightly below.
*Color*.—About Yellow Green Group — N144C.

Receptacle:
*Depth*.—Approximately 3.5 mm.
*Ovary diameter*.—1.25 mm average.
*Pubescence of inner surface*.—Absent.
*Pubescence of outer surface*.—Absent.

FOLIAGE DESCRIPTION

Leaves:
*Average length*.—Approx. 104 mm.
*Average width*.—Approx. 45 mm.
*Average thickness*.—Approx. 0.18 mm.
*Shape*.—Elliptic.
*Margin type*.—Bi-crenate.
*Leaf texture*.—Upper & Lower: Smooth.
*Leaf blade* (*ration of length to width*).—Elongated.
*Angle at apex*.—Acute.
*Leaf blade tip*.—Slightly curved downward.
*Color*.—Upper surface: About Green Group 135A.
*Color*.—Lower surface: About Green Group 136C.
*Base*.—Cuneate.
*Tip*.—Cuspidate.
*Venation*.—Reticulate.
*Vein color*.—Green Group — 135D.
*Shape in cross section*.—Flat.
*Profile*.—Flat.
*Undulation of margin*.—Bi-crenate.
*Density of pubescence of lower side*.—Sparse.
*Position of the nectaries*.—Predominantly on base of leaf blade.

Petiole:
*Average size* (*length*).—Approximately 15 mm.
*Average size* (*diameter*).—Approximately 1.4 mm.
*Surface texture*.—Smooth.
*Color*.—Upper side — Greyed orange group — 166A; Lower side — Green group — 138C.

Leaf glands:
*Average size*.—Approximately 1.10 mm×0.7 mm.
*Average number*.—Usually 2.
*Shape*.—Kidney shape.
*Color*.—Green group — 134C.
*Position*.—On base of the leaf.

Stipule:
*Texture*.—Smooth.
*Average length*.—Approximately 2 mm.
*Color*.—Greyed orange group — N167B.
*Persistence*.—Falls off.

FRUIT DESCRIPTION

General: 1st pick 18 January, 2nd pick 25 January.
*Maturity when described*.—Firm, 6-8 kg with 11 mm penetrometer probe.
*Season ripening*.—Mid-season.
*Position of maximum diameter*.—Middle of fruit.
*Symmetry about the suture*.—Symmetric.
*Shape of base*.—Depressed.

Size:
*Length* (*stem end to apex*).—Approximately 50 mm.
*Diameter perpendicular to suture plane*.—Approximately 55-65 mm.
*Diameter in line with suture plane*.—Approximately 49 mm.
*Average weight*.—Approximately 110 g.

Lenticel:
*Color*.—White Group, NN155B.
*Quantity*.—Many, Approximately 25-30 $cm^2$.

Form:
*Viewed from apex*.—Round, circular, symmetrical.
*Viewed from side, facing suture*.—Symmetric, rounded, truncate-to-depressed apex.
*Viewed from side, perpendicular to suture*.—Rounded, truncate-to-depressed apex, symmetrical.
*Apex shape*.—Truncate/Flattened.
*Apex base*.—Depressed.
*Suture line*.—Medium.

Fruit stem cavity:
*Shape*.—Flaring.
*Depth*.—Medium, approximately 9 mm.
*Breadth*.—Broad, approximately 20.9 mm.
*Width*.—Broad, approximately 16.5 mm.
Fruit stem:
*Length*.—Approximately 1.2 mm.
*Diameter*.—Approximately 1.1 mm.
*Color*.—Medium green, Yellow Green Group — 150C.
*Adherence to stone*.—Medium to weak.
Fruit skin:
*Thickness*.—Medium.
*Adherence to flesh*.—Medium.
*Surface texture*.—Smooth.
*Pubescence*.—Absent.
*Bloom*.—Present, Medium.
*Ground color*.—Yellow-green, 150A at harvest, Yellow Orange Group 23A after storage.
*Overcolor*.—Violet Blue Group 59A and 60A at harvest, Violet Blue Group N92A after storage.
*Relative area of overcolor*.—Large.
*Pattern of overcolor*.—Solid flush.
*Taste*.—Neutral.
*Reticulation*.—Absent.
*Roughness*.—Absent.
*Tenacity*.—Firm to flesh.
*Tendency to crack*.—Absent.
Flesh:
*Ripens*.—Evenly.
*Texture*.—Crisp-juicy.
*Fibers*.—Medium.
*Flavor*.—Neutral, sweet.
*Brix*.—Approximately 18-20°.
*Juice*.—Medium to abundant.
*Aroma*.—Slight.
*Color*.—Yellow-orange, 22C, turning into Orange Red Group N34B with ripening.
*Anthocyanin color around stone*.—Absent.
*Anthocyanin color of flesh*.—Medium.
*Acidity*.—Low to Medium — 2.35 g/100 ml.
*Sugar content*.—High, approximately 18-20° Brix.
*Eating quality*.—Very good.
*Stone*.—Flesh ratio: 1:60.
*Firmness*.—Firm to crisp texture.
Fruit shipping and keeping quality: Good, for four to eight weeks.
Fruit use: Fresh Market.
Stone:
*Stone freeness*.—Cling.
*Degree of adherence to flesh*.—Medium.
*Stone size*.—Medium.
*Length*.—Approximately 23 mm.
*Diameter in line with suture plan*.—Approximately 18.5 mm.
*Diameter perpendicular to suture plane*.—Approximately 11.5 mm.
*Width of stalk end*.—Medium.
*Angle of stalk end*.—Right angle.
*Size compared to fruit*.—Small.
*Hilum*.—Oval. Viewed from side: Narrow elliptic. Viewed from ventral end.: Medium elliptic.
*Shape*.—Flattened symmetrical.
*Base shape*.—Medium oval shape.
*Apex shape*.—Ovate with sharp point.
*Stone surface*.—Uneven/Irregular.
*Stone halves*.—Nearly symmetrical.
*Stone ridges*.—Present — Rough.
*Outgrowing keel*.—Well developed, asymmetrical.
*Stone tendency to split*.—No tendency observed.
*Stone color*.—Orange group — 165C.
Pit cavity size:
*Length*.—Approximately 15 mm.
*Diameter*.—Approximately 10 mm.
*Color*.—Orange Group 24D.
Kernel:
*Size*.—Length — Approximately 2 2 mm; Width — Approximately 16.9 mm.
*Shape*.—Narrow elliptic — Broadest part in the middle.
*Color*.—Greyed orange — N167B.

What is claimed is:

1. A new and distinct variety of plum tree having the characteristics substantially as described and illustrated herein.

* * * * *